United States Patent [19]

Drewlow

[11] Patent Number: Plant 7,258

[45] Date of Patent: Jul. 3, 1990

[54] KALANCHOE PLANT NAMED DESERT BLAZE

[75] Inventor: Lyndon W. Drewlow, Ashtabula, Ohio

[73] Assignee: Mikkelsens, Inc., Ashtabula, Ohio

[21] Appl. No.: 318,055

[22] Filed: Mar. 2, 1989

[51] Int. Cl.[5] ..... A01H 5/00

[52] U.S. Cl. ..... Plt./68

[58] Field of Search ..... Plt. 68

[56] References Cited

U.S. PATENT DOCUMENTS

P.P. 3,871 4/1976 Bull ..... Plt. 68
P.P. 3,872 4/1976 Bull ..... Plt. 68
P.P. 3,873 4/1976 Bull ..... Plt. 68
P.P. 4,101 9/1977 Grob ..... Plt. 68
P.P. 4,102 9/1977 Grob ..... Plt. 68
P.P. 5,962 4/1987 Mikkelsen ..... Plt. 68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Desert Blaze having growth characteristics to produce cut flowers. Desert Blaze has strong stems carrying crimson red flowers, tall, upright growth, good lateral branching, average flower and leaf size, and open inflorescence.

1 Drawing Sheet

The present invention relates to a new and distinctive cultivar of Kalanchoe plant, botanically known as *Kalanchoe blossfeldiana*, and known by the cultivar name Desert Blaze. The new cultivar was developed by me through controlled breeding by crossing Mikkelsen Seedlng No. 83-2272-1 (seed parent) with Mikkelsen Seedling No. 83-2297-1 (pollen parent). Both parents are unpatented. A principal objective of the breeding program was to develop new Kalanchoe cultivars having certain desired characteristics and which could be used to produce cut flowers.

Asexual reproduction of stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry. In order to describe the characteristics more meaningfully, references are made to known pot type Kalanchoe cultivars, including Attraction (U.S. Plant Pat. No. 5,888), Pollux (U.S. Plant Pat. No. 4,816), and Garnet, disclosed in my pending application. Also referred to are Passionate, Sombrero, Lemon Drop and Bashful, all cut flower type cultivars of applicant disclosed in pending plant applications.

1. Desert Blaze is an upright, tall cut flower type. Kalanchoe characterized by crimson flowers similar in color to the flowers of the pot type Kalanchoe plant Garnet, with Attraction and Pollux being more orange-red in color.

2. Desert Blaze is much taller (48–52 cm) than Garnet, Attraction and Pollux (all 18–22 cm without growth regulators), slightly taller than the cut flower types Sombrero and Passionate (both 43–47 cm), similar in height to Bashful (48–52 cm), and shorter than Lemon Drop (53–57 cm).

3. Desert Blaze has eight lateral branches similar to Lemon Drop and the three pot type comparisons, while Passionate, Bashful and Sombrero all generally have ten lateral branches.

4. Flower size of Desert Blaze is larger (16 mm) than Passionate, similar to Sombrero, Lemon Drop, Garnet, Pollux and Attraction, and smaller than Bashful (22 mm).

5. Leaves of Desert Blaze are smaller than Lemon Drop and Sombrero, similar in size to Garnet and Pollux, with Attraction, Bashful and Passionate having even smaller leaves.

6. Mature stigma of Desert Blaze has a reddish pink tint at the center of whitish area which is similar to Passionate, Bashful, and Garnet, with Attraction and Pollux having a very faint reddish pink area, and Lemon Drop and Sombrero having none.

7. Leaf margins of Desert Blaze are intermediate in their serration, with Pollux and Garnet being similar. Sombrero and Lemon Drop have only slight serration, and Attraction, Passionate and Bashful are more finely serrated.

8. The five cut flower type Kalanchoes tended to have very little basal branching from the lower two nodes, while the three pot type kalanchoe have much greater basal branching.

9. The inflorescence of Desert Blaze and the other four cut flower types is open with the flowers carried at the end of the long branches, while the pot types have a denser, more compact habit giving a mounded effect as the flowers are carried at the end of short stems.

10. Desert Blaze has very long lasting flowers that do not fade easily under high light or when flowers get older.

11. Strong stems to hold flowers.

12. Desert Blaze can be grown on a schedule to provide flowers each week of the year.

The accompanying colored photograph is a top perspective view, illustrating the overall appearance of Desert Blaze. The photograph shows colors as true as it is reasonably possible to obtain in a colored reproduction of this type.

The following is a detailed description of my new Kalanchoe cultivar based on plants produced under commercial practices in Ashtabula, Ohio, under greenhouse conditions. Color references are made to The Royal Horticulatural Society Colour Chart except where general color terms of ordinary dictionary significance are used.

The description is based on plant cuttings five (5) weeks old stuck in six (6) inch pots and given two (2) weeks of long days and then short days to induce flowering. The plants were grown at 64°-68° F. night temperatures. Measurements were taken twelve (12) weeks after the start of short days, with plant height being measured from the soil line of the plant.

PARENTAGE

A controlled cross between female parent Mikkelsen Seedling 83-2272-1 and male parent Mikkelsen Seedling 83-2297-1.

PROPAGATION (A) Type cutting: Stem tip cutting up to 3 cm long.
(A) Time to root: 10 days at 21° C. summer; 14 days at 21° C. winter.
(C) Rooting habit: Abundant, fine, fibrous roots.

PLANT DESCRIPTION (A) Form: Tall, upright, with flower clusters (inflorescence) carried above the main leaf mass on long stems; larger leaves near the base of the plant with smaller leaves in the flower cluster.
(B) Habit of growth: Upright, branching occurs from several nodes in the middle of the plant producing a spray form of flower cluster. Environment will play a role in how tall a plant will get.
(C) Foliage: Leaves simple and opposite.
(1) *Size.*—Average full grown leaf on a plant grown in a 15 mm pot is 130 mm long and 100 cm wide. Growth conditions will cause leaf size to vary.
(2) *Shape.*—Elliptic; apex obtuse; base is rounded.
(3) *Texture.*—Glabrous, coriaceous and succulent.
(4) *Margin.*—Crenate to dentate.
(5) *Color.*—Young foliage, top side near 137A; Young foliage, under side near 146B; Mature foliage, top side near 147A; Mature foliage, under side near 137B.

FLOWERING DESCRIPTION (A) Flowering habits: Inflorescence is a cyme. Terminal flower on main axis opens first followed by the terminal flowers on the side branches, continuing with subsequent development of branches in the inflorescence. Inflorescence is made up of the main stem and up to eight lateral branches. The inflorescence is 36–39 cm in height and 18–20 cm in diameter, and is open.
(B) Natural flowering season: Early January. Flowering time under controlled daylength at 20° C. in summer is nine weeks; in winter is twelve weeks. Flowering time depends on temperature, light intensity and other growing conditions. In general, higher temperatures (to the point of heat delay) and increased light intensity will speed up flowering, and low temperatures and light intensity will delay flowering. Other conditions that can cause delay in the flowering are low fertility, very high night temperatures (80° F. plus) and moisture stress.
(C) Flower buds: Oblong, up to 10 mm long just before showing first color, developing tubular as flower petals mature; sheath with four green sepals; corolla at maturity up to 10 mm long.
(D) Flower borne: Compound dichasial cymes, primary peduncle 6 mm in diameter just below the first branch of the inflorescence; length will vary depending on growing conditions. In general, peduncles will be shorter when the plants are moisture stressed, grown well spaced, grown under high light intensity, grown under low temperatures, or are given applications of growth regulators. If plants are grown crowded and/or under low light conditions, the peduncles will tend to stretch badly. Pedicels vary in length depending on where they are located in the inflorescence. The pedicels become shorter the higher they are in the inflorescence, that is, the closer thay are to the apical meristem.
(G) Reproductive organs:
(1) *Number of stamens.*—Eight. (a) Anther shape: Flat, elliptical; color — yellow green. (b) Filament color: Light green. (c) Pollen color: Yellow.
(2) Pistils.—(a) Stigma shape: Flat; color (immature) — greenish; color (mature) — white with reddish area in center. (b) Style color: Yellowish green. (c) Ovaries: Number — 4; size — 6 mm; color — green.

DISEASE RESISTANCE

Desert Blaze has shown good resistance to powdery mildew.

I claim:

1. A new and distinct cultivar of Kalanchoe plant named Desert Blaze, as illustrated and described.

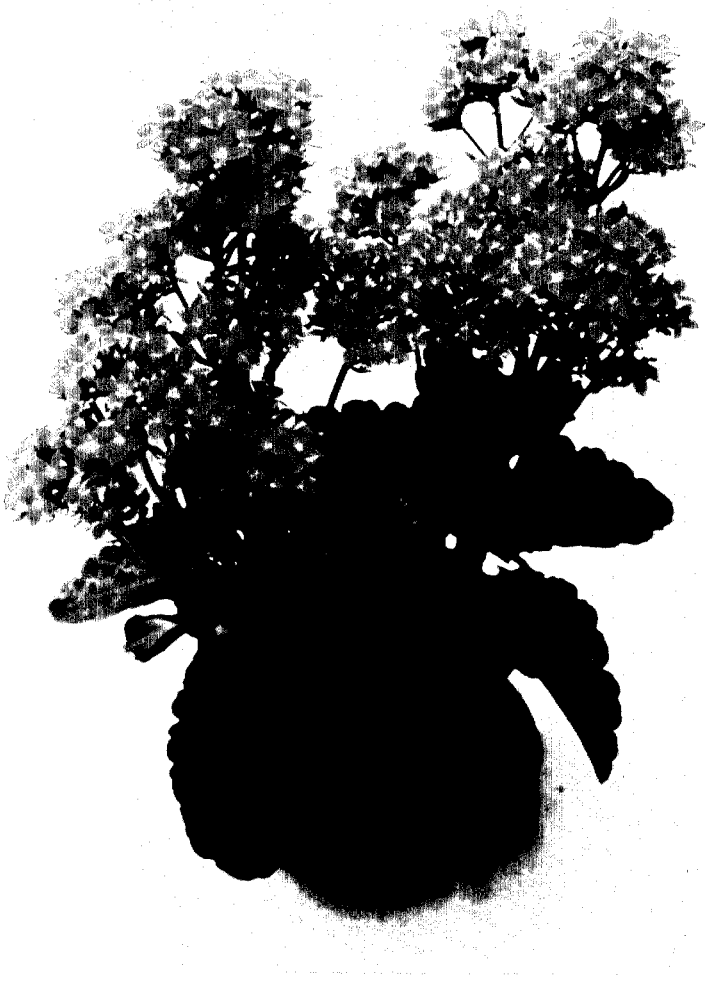

* * * * *